(12) United States Patent
Nakamura

(10) Patent No.: US 8,564,312 B2
(45) Date of Patent: Oct. 22, 2013

(54) FUEL SENSOR

(75) Inventor: Hiroshi Nakamura, Nishio (JP)

(73) Assignee: Denso Corporation, Kariya (JP)

( * ) Notice: Subject to any disclaimer, the term of this patent is extended or adjusted under 35 U.S.C. 154(b) by 202 days.

(21) Appl. No.: 13/293,405

(22) Filed: Nov. 10, 2011

(65) Prior Publication Data

US 2012/0126835 A1 May 24, 2012

(30) Foreign Application Priority Data

Nov. 18, 2010 (JP) .................... 2010-257756

(51) Int. Cl.
*G01L 23/22* (2006.01)
*G01R 19/00* (2006.01)

(52) U.S. Cl.
USPC .............. 324/663; 73/35.01; 324/76.11

(58) Field of Classification Search
USPC .............. 324/663, 76.11; 73/35.01–35.13
See application file for complete search history.

(56) References Cited

U.S. PATENT DOCUMENTS 6,431,147 B1 * 8/2002 Hiraiwa et al. ............... 123/458
2009/0193873 A1 8/2009 Nakamura et al.

FOREIGN PATENT DOCUMENTS

JP P2010-210563 A 9/2010

OTHER PUBLICATIONS

Japanese Official Action dated Nov. 2, 2012 issued in corresponding Japanese Application No. 2010-257756, with English translation.

* cited by examiner

*Primary Examiner* — Jermele M Hollington
*Assistant Examiner* — Farhana Hoque
(74) *Attorney, Agent, or Firm* — Nixon & Vanderhye P.C.

(57) ABSTRACT

An outer electrode projects from an opening, which is formed in an upper inner wall of a fuel passage, into the fuel passage. The fuel passage is adapted to conduct fuel generally in a horizontal direction. The outer electrode includes a fuel chamber in an inside of the outer electrode. An inner electrode is placed in the fuel chamber. A sensing circuit senses an alcohol concentration of the fuel based on an electrical property between the outer electrode and the inner electrode and a fuel temperature, which is sensed with a thermistor. The outer electrode includes a blocking portion and communication holes. The blocking portion limits intrusion of air bubbles, which flow along the upper inner wall of the fuel passage, into the communication holes.

6 Claims, 7 Drawing Sheets

FUEL SENSOR

CROSS REFERENCE TO RELATED APPLICATION

This application is based on and incorporates herein by reference Japanese Patent Application No. 2010-257756 filed on Nov. 18, 2010.

BACKGROUND OF THE INVENTION

1. Field of the Invention

The present invention relates to a fuel sensor, which senses a property of fuel.

2. Description of Related Art

A fuel sensor is placed in a fuel supply system, which supplies fuel to an internal combustion engine. The fuel sensor senses a property of the fuel, such as an alcohol concentration of the fuel, a pressure of the fuel or an oxidation state of the fuel.

For example, WO 00/73646A1 (corresponding to U.S. Pat. No. 6,431,147B1) recites a fuel pressure regulator, which serves as a fuel sensor that senses the fuel pressure. This fuel pressure regulator includes a pressure detector portion that is placed in the fuel passage, through which the fuel discharged from the fuel pump flows. The fuel pressure regular controls an electric current, which is supplied to an electric motor of a fuel pump, based on a fuel pressure that is applied to the pressure detector portion.

In a case where the temperature of the fuel, which flows through the fuel passage, becomes high, and thereby the fuel pressure becomes lower than a saturation vapor pressure that corresponds to the temperature of the fuel, air bubbles are generated in the fuel. Furthermore, when the air bubbles, which are contained in the return fuel that is returned from the internal combustion engine to the fuel tank, are drawn into a fuel pump, the fuel, which contains the air bubbles, is discharged from the outlet of the fuel pump.

The fuel passage, which is provided in the fuel pressure regulator of WO 00/73646A1 (corresponding to U.S. Pat. No. 6,431,147B1), extends in the vertical direction. The pressure detector portion of the fuel pressure regulator is provided at an upper portion of the fuel passage in the vertical direction. Therefore, the air bubbles of the fuel may possibly be drawn into and stagnated in the pressure detector portion. When this happens, the pressure of the fuel cannot be accurately sensed with the pressure detector, thereby resulting in an sensing error of the fuel pressure.

SUMMARY OF THE INVENTION

The present invention addresses the above disadvantage.

According to the present invention, there is provided a fuel sensor, which includes an outer electrode, an inner electrode, temperature sensing means and a sensing circuit. The outer electrode projects from an opening, which is formed in an upper inner wall of a fuel passage, into the fuel passage. The fuel passage is adapted to conduct fuel generally in a horizontal direction, and the outer electrode includes a fuel chamber in an inside of the outer electrode. The inner electrode is placed in the fuel chamber of the outer electrode. The temperature sensing means is for sensing a fuel temperature of the fuel in the fuel chamber. The sensing circuit senses a fuel property of the fuel based on an electrical property between the outer electrode and the inner electrode and the fuel temperature, which is sensed with the temperature sensing means. The outer electrode includes a blocking portion and at least one communication hole. The blocking portion is configured into a tubular form and is placed on a lower side of the upper inner wall of the fuel passage. The at least one communication hole is placed on a lower side of the blocking portion and communicates between the fuel chamber and the fuel passage. The blocking portion is adapted to limit intrusion of air bubbles, which flow along the upper inner wall of the fuel passage, into the at least one communication hole.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF THE INVENTION

Various embodiments of the present invention will be described with reference to the accompanying drawings.

First Embodiment

FIGS. 1 to 4 show a fuel sensor according to a first embodiment of the present invention. The fuel sensor 1 of the present embodiment is a concentration sensor, which is placed in a fuel supply system of a vehicle (e.g., an automobile) and senses an ethanol concentration of fuel. A measured value of the ethanol concentration, which is measured with the fuel sensor 1, is transmitted to an electronic control unit (ECU). The ECU controls a fuel injection quantity of each corresponding injector and ignition timing of the fuel for an internal combustion engine based on the measured value of the ethanol concentration. In this way, an air-fuel ratio of the internal combustion engine becomes an appropriate value, and a drivability of the vehicle becomes appropriate. Also, noxious components of the exhaust gas are reduced.

Now, a fuel supply apparatus 10, to which the fuel sensor 1 is installed, will be described.

Figure 1:
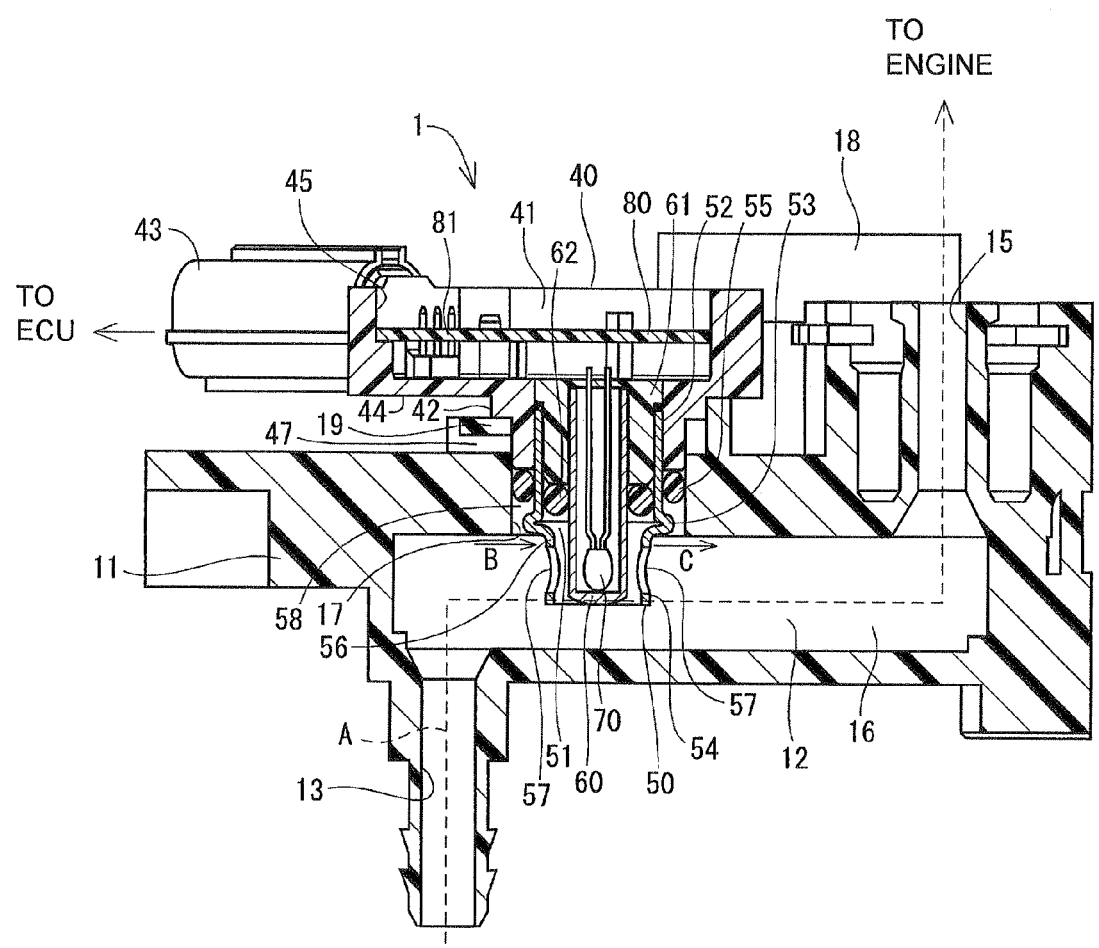
FIG. 1 is a cross-sectional view of a fuel sensor according to a first embodiment of the present invention.
Figure 2:
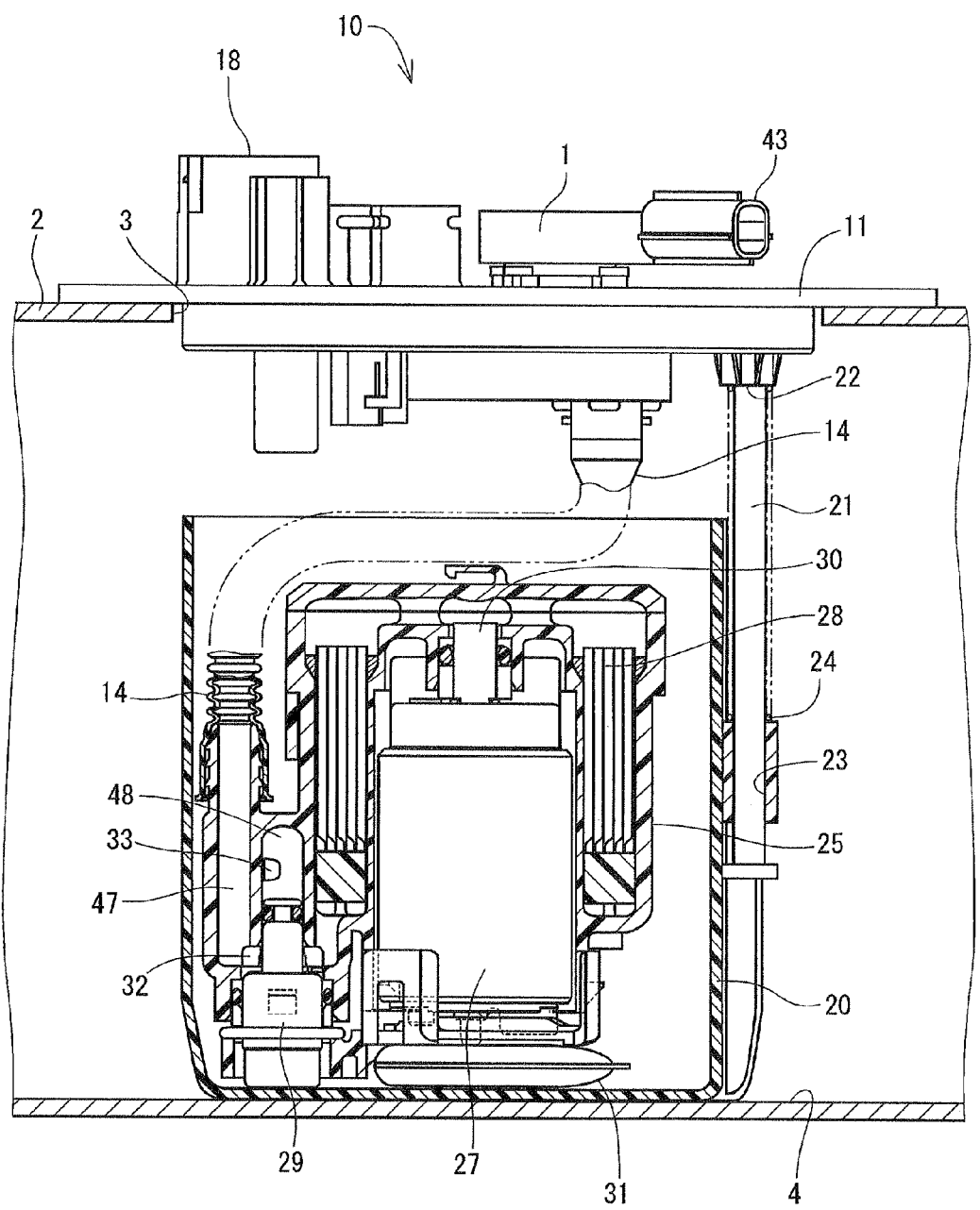
FIG. 2 is a cross-sectional view of a fuel supply apparatus, to which the fuel sensor of the first embodiment is installed.

As shown in FIGS. 1 and 2, the fuel supply apparatus 10 includes a flange 11, a sub-tank 20, a pump body 25, a pump main body 27, a filter 28, a pressure regulator 29 and the fuel sensor 1.

The flange 11 is configured into a generally circular disk and closes an opening 3, which is formed in an upper wall of a fuel tank 2. A fuel passage 12 is formed in the flange 11 to conduct fuel, which is discharged from the pump main body 27. One end portion 13 of the fuel passage 12 extends generally in a vertical direction (a direction of gravity at the time when the vehicle is parked on a horizontal ground that extends in the horizontal plane) in an inside of the fuel tank 2. In other words, the one end portion 13 of the fuel passage 12 extends in a direction (vertical direction) generally perpendicular to a plane of the flange 11 or in a direction (vertical direction) generally perpendicular to a plane of a bottom wall 4 of the fuel tank 2. A bellows tube (flexible tube) 14 is connected to the one end portion 13 of the fuel passage 12.

The other end portion 15 of the fuel passage 12, which is opposite from the one end portion 13, extends generally in the vertical direction at an outside of the fuel tank 2. A fuel conduit (not shown) is connected to the other end portion 15 of the fuel passage 12. The fuel is supplied to the internal combustion engine through the fuel conduit.

A flow passage section 16 of the fuel passage 12, which is located between the one end portion 13 and the other end portion 15 in the fuel passage 12, extends generally in a horizontal direction (a direction perpendicular to the vertical direction discussed above or a direction generally parallel to the plane of the flange 11 or generally parallel to the plane of the bottom wall 4 of the fuel tank 2) along the flange 11. An opening 17 is formed in an upper inner wall of the flow passage section 16 of the fuel passage 12, which extends generally in the horizontal direction. The opening 17 is formed at a corresponding location, which is spaced by a predetermined distance from a vertically extending flow passage section of the one end portion 13 of the fuel passage 12. In the fuel passage 12 having the opening 17, as indicated by a dotted line A in FIG. 1, the fuel, which flows vertically in the one end portion 13, changes a flow direction thereof and flows generally in the horizontal direction. At this time, air bubbles, which are contained in the fuel, flow along the upper inner wall of the flow passage section 16 of the fuel passage 12. The flow passage section 16 of the fuel passage 12 extends generally in the horizontal direction to the extent that it enables flow of the air bubbles, which are generated in the fuel, along the upper inner wall of the fuel passage 12. In other words, the flow passage section 16 may extend in a direction that is tilted relative to the horizontal direction as long as the air bubbles can flow along the upper inner wall of the fuel passage 12 (more specifically, the upper inner wall of the flow passage section 16) toward the other end portion 15 of the fuel passage 12.

The fuel sensor 1 is installed in the opening 17 of the fuel passage 12. The fuel sensor 1 will be described in detail later.

An electric connector 18 is formed in the flange 11. The electric connector 18 supplies an electric power to an electric motor of the pump main body 27.

The sub-tank 20 is configured into a cup shape body (a tubular body having a bottom) and is inserted into the fuel tank 2. A support shaft 21 connects between the flange 11 and the sub-tank 20. One end portion of the support shaft 21 is press fitted into a mount hole 22, which is formed in the flange 11, and the other end portion of the support shaft 21 is slidably received in a hole 23, which is formed in the sub-tank 20. A compression coil spring 24 is installed around an outer peripheral surface of the support shaft 21 to exert a resilient force and thereby to urge the sub-tank 20 against the bottom wall 4 of the fuel tank 2.

The pump body 25 is received in an inside of the sub-tank 20. The pump body 25 is fixed to the sub-tank 20 with a fitting member (not shown).

The pump body 25 receives the pump main body 27, the filter 28 and the pressure regulator 29.

The pump main body 27 is configured into a generally cylindrical body and contains the electric motor (not shown) and an impeller (not shown) driven by the electric motor. When the impeller is rotated, the pump main body 27 draws the fuel through an inlet thereof, which is formed at an axial lower side, and then discharges the fuel through an outlet 30 thereof, which is formed at an axially upper side, upon pressurizing the same.

A suction filter 31 is placed at the inlet of the pump main body 27. The suction filter 31 is a bag-type filter and captures relatively large contaminants contained the fuel to be drawn from the sub-tank 20 into the pump main body 27 through the inlet thereof.

The filter 28 is placed on a radially outer side of the pump main body 27. A filter element of the filter 28 is configured into a tubular form and captures relatively small contaminants contained in the fuel to be discharged from the outlet 30 of the pump main body 27.

The pressure regulator 29 is placed in a passage 32, which is located on a downstream side of the filter 28. The pressure regulator 29 adjusts a pressure of the fuel, which flows in the passage 32. The pressure regulator 29 discharges the excess fuel, which becomes excessive at the time of adjusting the pressure, into the sub-tank 20 through an opening 33.

The fuel, which is discharged from the pump main body 27 and has the pressure adjusted through the pressure regulator 29, passes through the bellows tube 14, the fuel passage 12 of the flange 11 and the fuel conduit and is supplied to the internal combustion engine (or simply referred to as the engine).

Figure 3:
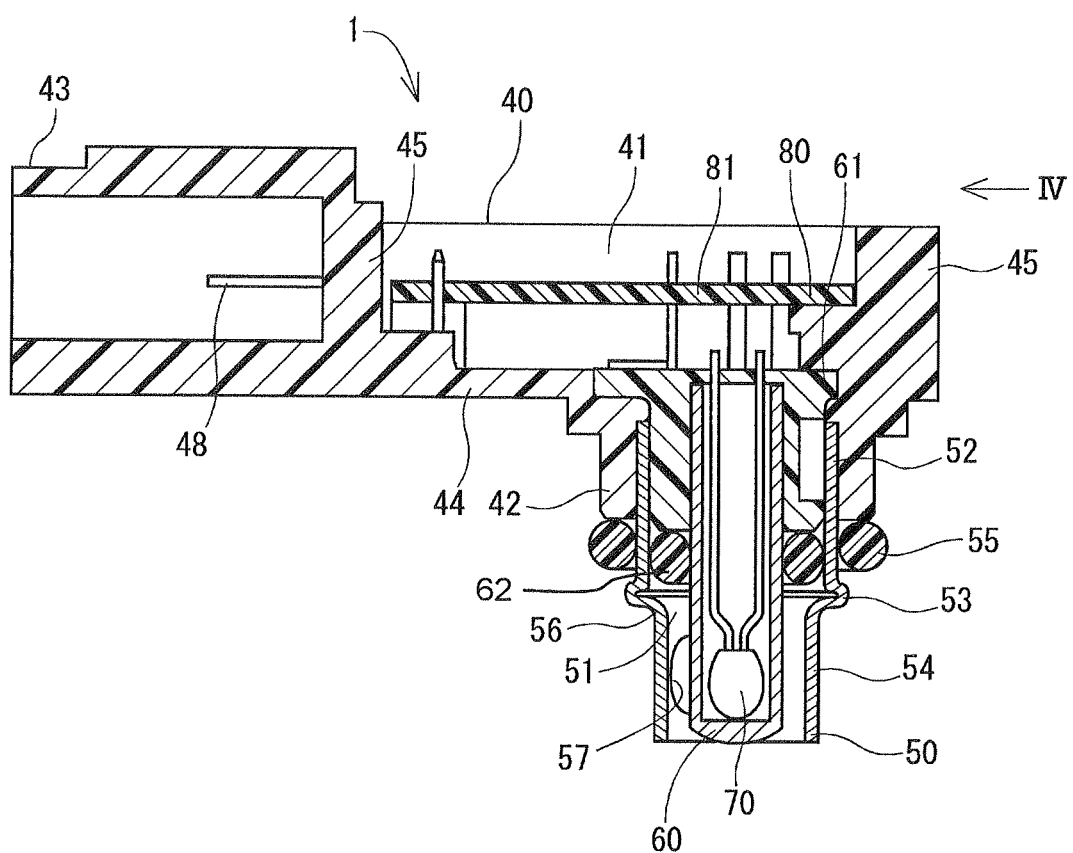
FIG. 3 is a cross sectional view of the fuel sensor of the first embodiment.
Figure 4:
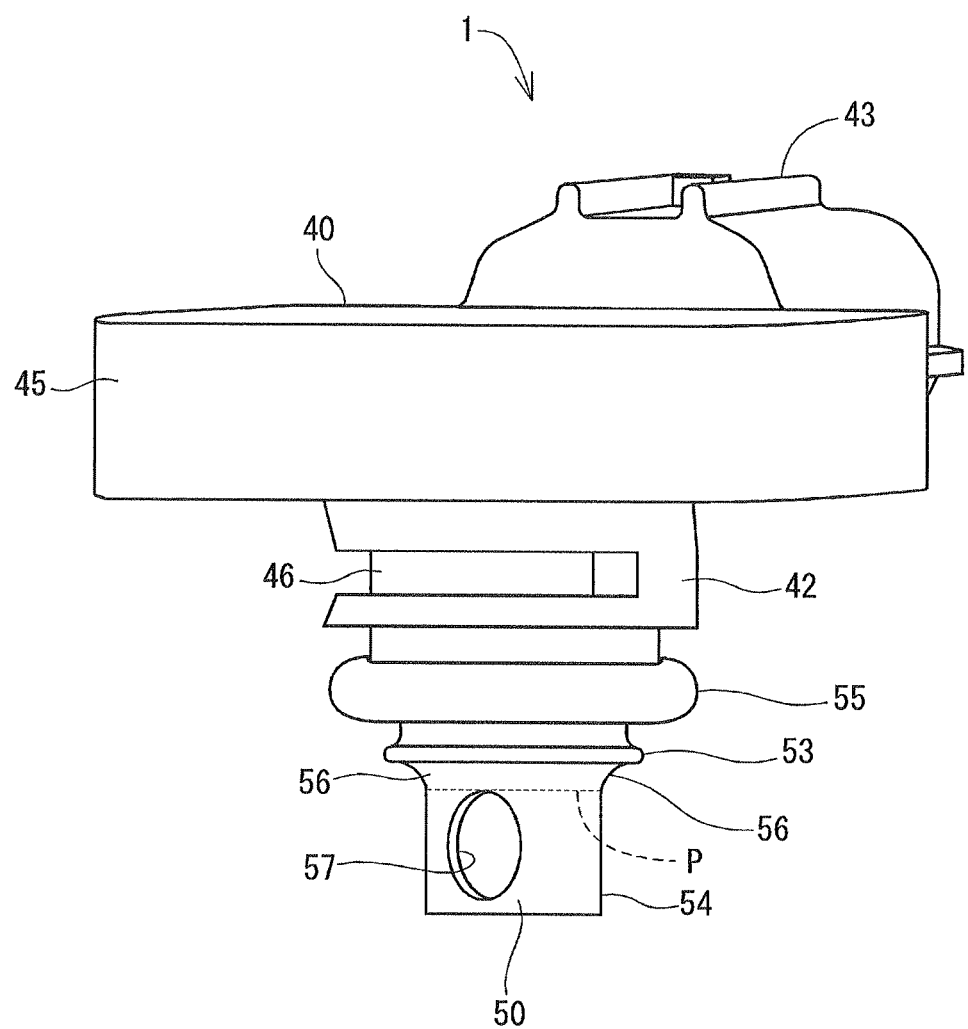
FIG. 4 is a view taken in a direction of an arrow IV in FIG. 3.

Next, the fuel sensor 1 will be described with referent FIGS. 1, 3 and 4.

The fuel sensor 1 includes a housing 40, an outer electrode 50, an inner electrode 60, a thermistor 70 and a circuit board 80.

The housing 40 is made of, for example, resin and has a circuit board receiving portion 41, a cylindrical tubular portion 42 and a connector 43. The circuit board receiving portion 41 is configured into a cup shape body (a tubular body having a bottom) and has a bottom portion 44 and a peripheral portion 45. The circuit board 80, on which a sensing circuit 81 is formed, is installed to the inside of the circuit board receiving portion 41 with, for example, screws.

The cylindrical tubular portion 42 extends from the bottom portion 44 of the circuit board receiving portion 41 toward the fuel passage 12. A groove 46 is formed in an outer peripheral wall of the cylindrical tubular portion 42. A projection 19 radially outwardly projects from the opening 17 of the flange 11. A clip 47 is fitted into the groove 46 (see FIG. 4) of the cylindrical tubular portion 42 from a radially outer side of the projection 19. In this way, the housing 40 is fixed to the flange 11.

The connector 43 is formed in the peripheral portion 45 of the circuit board receiving portion 41. Terminals 48 of the connector 43 are electrically connected to the ECU (not shown).

The outer electrode 50 is configured into a cylindrical tubular body through press working of a metal plate made of, for example, stainless steel. The outer electrode 50 is electrically connected to the sensing circuit 81 of the circuit board 80. One end portion of the outer electrode 50 is resin molded in the cylindrical tubular portion 42 of the housing 40, and the other end portion of the outer electrode 50 extends into the fuel passage 12. The outer electrode 50 includes a fuel chamber 51, which is defined on a radially inner side of the portion of the outer electrode 50, which is inserted into the fuel passage 12.

The outer electrode 50 has a large diameter portion 52, an annular portion 53 and a small diameter portion 54, which are arranged in this order from the upper side of the outer electrode 50. The large diameter portion 52 has a diameter, which is larger than that of the small diameter portion 54. An annular outer seal member 55 is placed between an inner wall of the opening 17 of the flange 11 and the large diameter portion 52. The outer seal member 55 is made of, for example, an O-ring and limits leakage of the fuel through a gap between the opening 17 of the flange 11 and the large diameter portion 52.

The annular portion 53 is configured into an annular form and radially outwardly protrudes at a location between the large diameter portion 52 and the small diameter portion 54. The annular portion 53 limits falling off of the outer seal member 55 from the large diameter portion 52.

The small diameter portion 54 includes a blocking portion 56, which is configured into a tubular form and is placed on a lower side of the annular portion 53. Although a lower boundary of the blocking portion 56 is schematically indicated with a dotted line P in FIG. 4, the annular portion 53 is formed integrally with the outer electrode 50.

The small diameter portion 54 includes two communication holes 57, which communicate between the fuel passage 12 and the fuel chamber 51. The communication holes 57 are symmetrically arranged one after another in the flow direction of the fuel in the fuel passage 12 and are symmetrical about the axis of the outer electrode 50. Thereby, the flow of the fuel in the fuel chamber 51 is facilitated.

An axial length of the blocking portion 56 is set by conducting, for example, experiments based on the amount of bubbles, which flow in the fuel passage 12. Specifically, the axial length of the blocking portion 56, which is measured in the axial direction of the outer electrode 50, is increased when the amount of the air bubbles, which flow in the fuel passage 12, is increased. In contrast, the axial length of the blocking portion 56 is decreased when the amount of the bubbles, which flow in the fuel passage 12, is decreased. The axial length of the blocking portion 56 is set to an appropriate length that can limit the intrusion of the air bubbles, which flow along the upper inner wall of the fuel passage 12, into the communication holes 57.

An inner diameter of the opening 17 of the fuel passage 12 is larger than an outer diameter of the annular portion 53. Thereby, a reservoir space 58 is formed between the inner wall of the opening 17 of the fuel passage 12 and the outer wall of the outer electrode 50 and is adapted to receive, i.e., take the fuel. The reservoir space 58 is located on a lower side of the outer seal member 55 and circumferentially extends all around the outer electrode 50 on the radially outer side of the outer electrode 50.

The air bubbles, which flow along the upper inner wall of the fuel passage 12 (more specifically, the flow passage section 16), flow along the outer peripheral surface of the blocking portion 56 while bypassing the communication holes 57 and thereafter flow to the downstream side of the outer electrode 50. Therefore, intrusion of the air bubbles into the fuel chamber 51 through the communication holes 57 can be limited.

Furthermore, some of the air bubbles, which flow along the upper inner wall of the fuel passage 12, flow into the reservoir space 58 before reaching to the outer electrode 50. Therefore, these air bubbles, which enter the reservoir space 58, flow through the reservoir space 58 and exit from the reservoir space 58 to the fuel passage 12 on the downstream side of the reservoir space 58. The air bubbles, which flow through the reservoir space 58, are limited from entering the communication holes 57 by the annular portion 53.

The inner electrode 60 is made of metal (e.g., stainless steel) and is configured into a tubular body having a bottom. The inner electrode 60 is resin molded in an inner peripheral portion of a holder 61, which is made of resin and is configured into a cylindrical tubular body. The inner electrode 60 is electrically connected to the sensing circuit 81 of the circuit board 80.

The holder 61 is inserted into an inside of the large diameter portion 52 of the outer electrode 50 and is fixed to the bottom portion 44 and the cylindrical tubular portion 42 of the housing 40 through, for example, swaging of the large diameter portion 52 against the holder 61 and/or the welding (or fusing). The inner electrode 60 is placed in the fuel chamber 51, which is formed in the inside of the outer electrode 50, such that the inner electrode 60 is generally coaxial with the outer electrode 50. Thereby, the outer electrode 50 and the inner electrode 60 function as a capacitor, in which the fuel serves as a dielectric material.

An inner seal member 62, which is configured into an annular form, is placed between the outer electrode 50 and the inner electrode 60. The inner seal member 62 is made of an O-ring and limits leakage of the fuel into the circuit board receiving portion 41 of the housing 40 through a gap between the outer electrode 50 and the inner electrode 60.

The large diameter portion 52 is formed in the housing 40 side portion of the outer electrode 50. Therefore, the gap between the large diameter portion 52 and the inner electrode 60 becomes larger than the gap between the small diameter portion 54 and the inner electrode 60. In this way, it is possible to reduce or minimize influence of a stray capacitance, which is generated between the outer electrode 50 and the inner electrode 60 due to the presence of the holder 61 and the inner seal member 62, on the measurement of the capacitance of the fuel in the fuel chamber 51.

The thermistor 70, which serves as temperature sensing means, is received in the inner electrode 60 on the radially inner side of the inner electrode 60. The thermistor 70 is electrically connected to the sensing circuit 81 of the circuit board 80. A heat conductive material (not shown), which is made of, for example, silicon, is received in the inside of the inner electrode 60. In this way, the temperature of the fuel in the fuel chamber 51 is conducted to the thermistor 70 through the wall of the inner electrode 60 and the heat conductive material.

The sensing circuit 81, which is formed in the circuit board 80, is electrically connected to the outer electrode 50, the inner electrode 60 and the thermistor 70. A potting material (not shown) is filled in a space located on the upper side of the circuit board 80. The sensing circuit 81 senses the capacitance between the outer electrode 50 and the inner electrode 60 through the charging and discharging between the outer electrode 50 and the inner electrode 60. The sensing circuit 81 senses the fuel temperature of the fuel chamber 51 through the thermistor 70. The value of the capacitance changes depending on a dielectric constant of the fuel. The dielectric constant of the fuel changes depending on a mixing ratio between the gasoline and ethanol of the fuel and the fuel temperature. Therefore, the sensing circuit 81 senses the ethanol concentration of the fuel in the fuel chamber 51 based on the capacitance between the electrodes 50, 60 and the fuel temperature. The ethanol concentration, which is sensed with the sensing circuit 81, is transmitted to the ECU through the corresponding terminal 48 of the connector 43. The ECU appropriately controls the air-fuel ratio of the internal combustion engine by controlling the fuel injection quantity of each corresponding fuel injector and the ignition timing of the fuel based on the ethanol concentration.

Now, the advantages of the present embodiment will be described.

(1) The fuel passage 12 (more specifically, the flow passage section 16) of the fuel sensor 1 is formed to extend generally in the horizontal direction. Therefore, the air bubbles, which are contained in the fuel that flows through the fuel passage 12, flow along the upper inner wall of the fuel passage 12 (more specifically, the flow passage section 16). The outer electrode 50 includes the blocking portion 56, which is configured into the tubular form and is placed on the lower side of the upper inner wall of the fuel passage 12. Furthermore, the outer electrode 50 includes the communication holes 57 on the lower side of the blocking portion 56. Therefore, the air bubbles, which flow the fuel passage, flow along the outer peripheral surface of the blocking portion 56 while bypassing the communication holes 57, and thereby it is possible to limit the intrusion of the air bubbles into the fuel chamber 51 through the communication holes 57. As a result, the sensing circuit 81 can sense the capacitance between the outer electrode 50 and the inner electrode 60 without being influence by the air bubbles. Thus, the sensing accuracy of the fuel sensor 1 can be increased.

(2) In the present embodiment, the reservoir space 58 is formed between the inner wall of the opening 17 of the fuel passage 12 and the outer wall of the outer electrode 50. Furthermore, the outer electrode 50 includes the annular portion 53, which radially outwardly protrudes from the blocking portion 56. Thereby, some of the air bubbles, which flow the fuel passage 12, flow into the reservoir space 58 before reaching to the outer electrode 50. The air bubbles, which enter the reservoir space 58, flow through the reservoir space 58 and exit from the reservoir space 58 into the fuel passage 12 on the downstream side of the reservoir space 58. The intrusion of the air bubbles, which flow through the reservoir space 58, into the communication holes 57, is limited by the annular portion 53. Therefore, the amount of the air bubbles, which flow along the outer peripheral surface of the blocking portion 56, is reduced, and thereby the intrusion of the air bubbles from the communication holes 57 into the fuel chamber 51 is limited. Thus, the sensing accuracy of the fuel sensor 1 can be increased.

Second Embodiment

Figure 5:
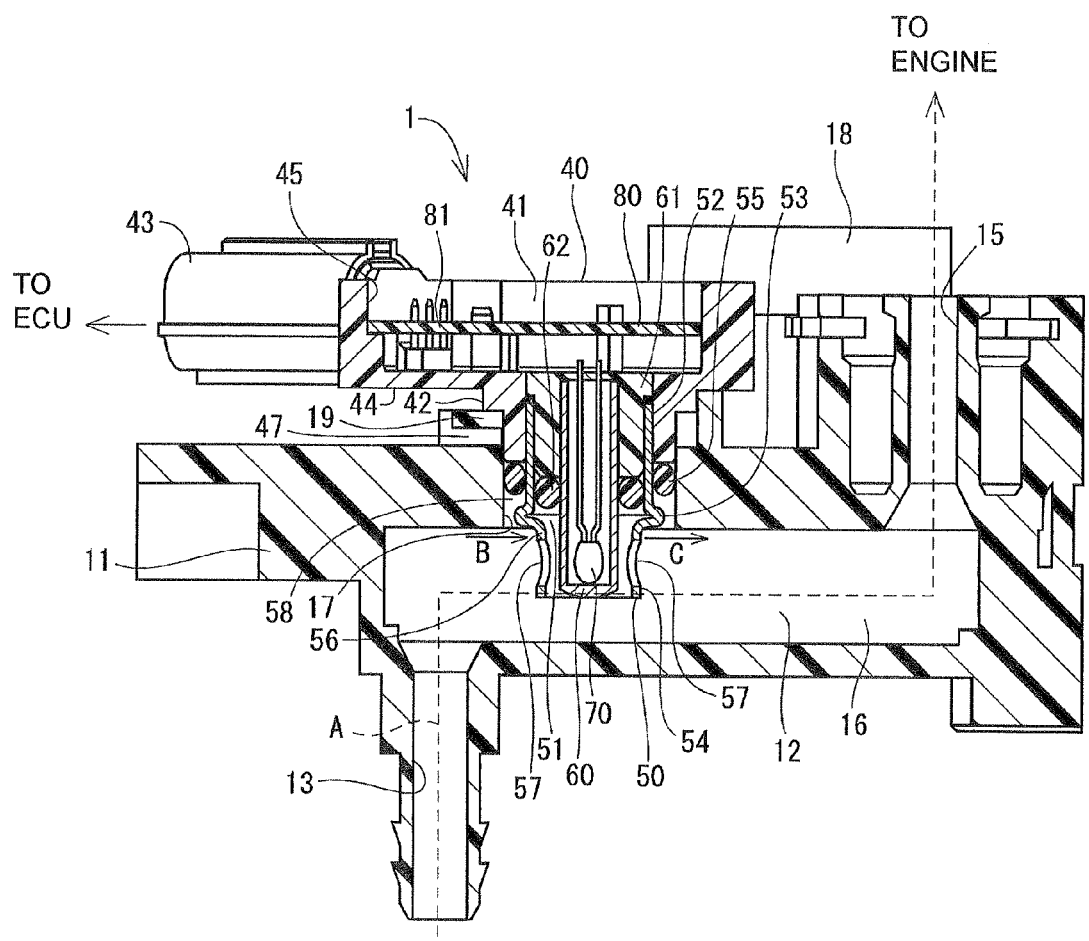
FIG. 5 is a cross sectional view of a fuel sensor according to a second embodiment of the present invention.

A fuel sensor according to a second embodiment of the present invention will be described with reference to FIG. 5. In the following embodiments, the components, which are similar to those of the first embodiment, will be indicated by the same reference numerals and will not be described again for the sake of simplicity. In the fuel sensor 1 of the present embodiment, an enlarged diameter portion 59, which is configured into a cylindrical form, is formed in the inner peripheral wall of the opening 17 of the fuel passage 12. An inner diameter of the enlarged diameter portion 59 is larger than an inner diameter of the opening 17. In this way, the volume of the reservoir space 58 can be increased. Thus, as indicated by arrows D, E in FIG. 5, the amount of the air bubbles, which flow in the reservoir space 58, is increased. Thus, the amount of the air bubbles, which flow along the outer peripheral surface of the blocking portion 56, is reduced, and thereby it is possible to more reliably limit the intrusion of the air bubbles into the fuel chamber 51 through the communication holes 57 and the stagnation of the air bubbles in the fuel chamber 51.

Third Embodiment

Figure 6:
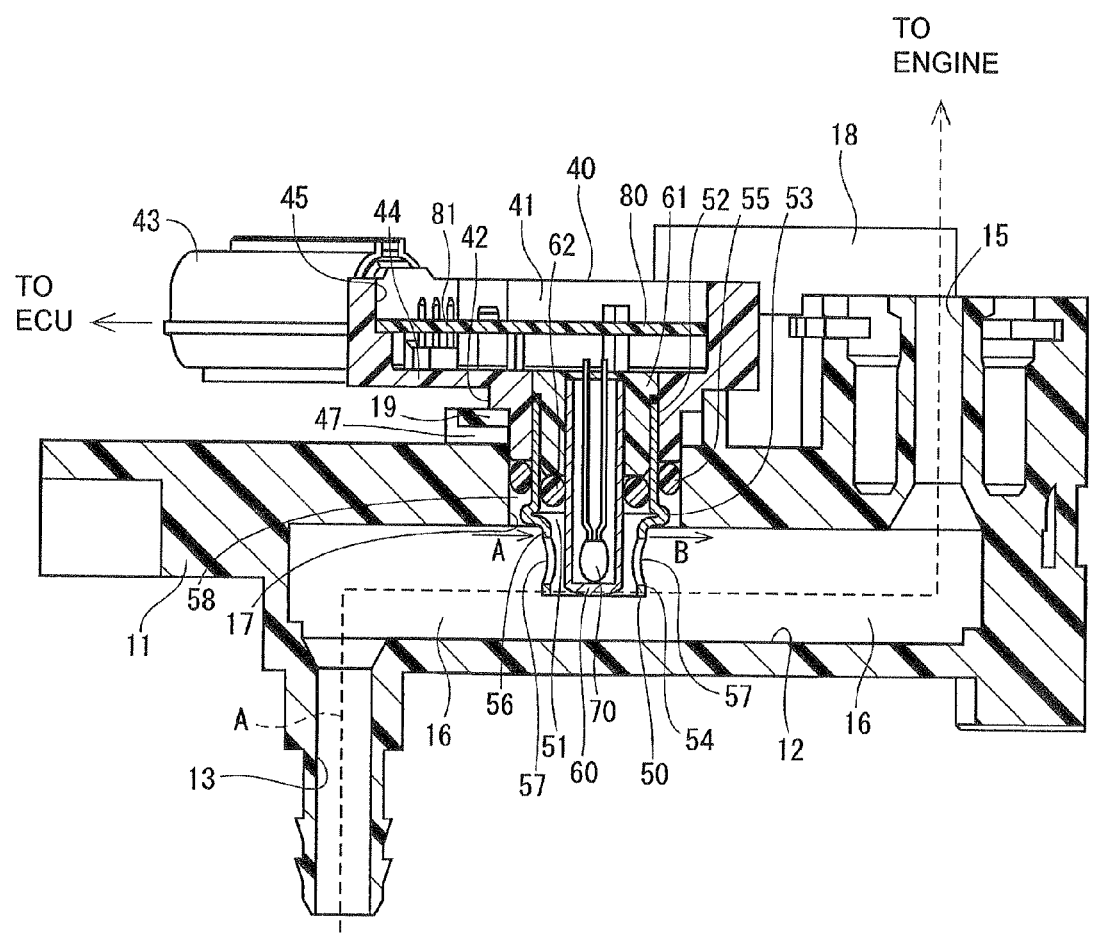
FIG. 6 is a cross sectional view of a fuel sensor according to a third embodiment of the present invention.

A fuel sensor according to a third embodiment of the present invention will be described with reference to FIG. 6. In the present embodiment, the flow passage section 16 of the fuel passage 12, which extends generally in the horizontal direction, is lengthened in comparison to the flow passage section 16 of the first or second embodiment. The fuel sensor 1 is placed at a location, which is more distant from the one end portion 13 of the fuel passage 12 that is connected to the bellows tube 14. In this way, the fuel, which flows upward in the vertical direction from the bellows tube 14, flows through the flow passage section 16 upon changing its flow direction to the horizontal direction. At this time, the air bubbles, which are contained in the fuel, can reliably flow along the upper inner wall of the fuel passage 12 (more specifically, the flow passage section 16). The air bubbles, which flow along the upper inner wall of the fuel passage 12, are limited from entering into the communication holes 57 after flowing along the outer peripheral surface of the blocking portion 56. Thereby, it is possible to limit the intrusion of the air bubbles into the fuel chamber 51 and the stagnation of the air bubbles in the fuel chamber 51.

Fourth Embodiment

Figure 7:
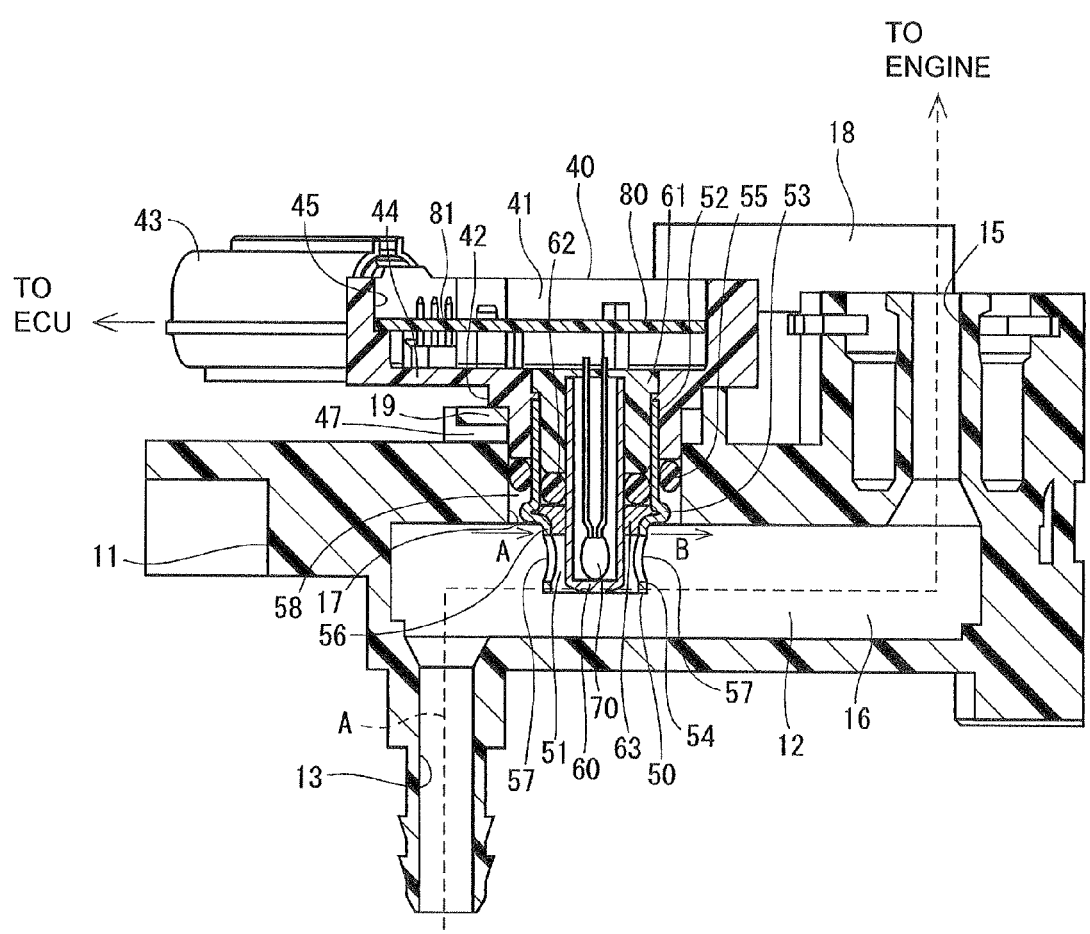
FIG. 7 is a cross-sectional view of a fuel sensor according to a fourth embodiment of the present invention.

A fuel sensor according to a fourth embodiment of the present invention will be described with reference to FIG. 7. In the present embodiment, an annular spacer 63 is installed between the outer electrode 50 and the inner electrode 60. The spacer 63 is made of a dielectric material and is placed in a plane, in which an upper end of each communication hole 57 is located. In this way, even in a case where the air bubbles flow into the fuel chamber 51, the air bubbles flow along a lower surface of the spacer 63 and immediately exit from the communication hole 57 into the fuel passage 12 on the downstream side of the outer electrode 50. Therefore, the sensing accuracy of the fuel sensor 1 can be improved.

Now, modifications of the above embodiments will be described.

In the above embodiments, the concentration sensor, which senses the ethanol concentration of the fuel based on the electric property between the electrodes, is described as the fuel sensor. Alternatively, the present invention may be applied to a fuel sensor, which senses a state of oxidization/degradation of the fuel based on an electric property between the electrodes.

In the fuel sensor of the above embodiments, the capacitance between the electrodes is sensed to sense the property and the state of the fuel based on the dielectric constant of the fuel. Alternatively, the fuel sensor of the present invention may sense a resistance between the electrodes to sense a property and a state of fuel based on an electrical conductivity of the fuel.

As discussed above, the fuel sensor of each of the above embodiments is installed to the fuel passage, which is formed in the flange of the fuel supply apparatus. Alternatively, the fuel sensor of the present invention may be installed to any other fuel passage, which conducts the fuel generally in the horizontal direction, in the fuel supply system that supplies the fuel to the internal combustion engine.

The present invention is not limited the above embodiments and modifications thereof. That is, the above embodiments and modifications thereof may be modified in various ways without departing from the sprit and scope of the invention.

What is claimed is:
1. A fuel sensor comprising:
an outer electrode that projects from an opening, which is formed in an upper inner wall of a fuel passage, into the fuel passage, wherein the fuel passage is adapted to conduct fuel generally in a horizontal direction, and the outer electrode includes a fuel chamber in an inside of the outer electrode;

an inner electrode that is placed in the fuel chamber of the outer electrode;

temperature sensing means for sensing a fuel temperature of fuel in the fuel chamber; and a sensing circuit that senses a fuel property of the fuel based on:

an electrical property between the outer electrode and the inner electrode; and the fuel temperature, which is sensed with the temperature sensing means, wherein:

the outer electrode includes:

a blocking portion, which is configured into a tubular form and is placed on a lower side of the upper inner wall of the fuel passage; and at least one communication hole, which is placed on a lower side of the blocking portion and communicates between the fuel chamber and the fuel passage; and the blocking portion is adapted to limit intrusion of air bubbles, which flow along the upper inner wall of the fuel passage, into the at least one communication hole.

2. The fuel sensor according to claim 1, wherein the blocking portion is configured into a tubular form, which has an axis that is generally perpendicular to a flow direction of the fuel in the fuel passage.

3. The fuel sensor according to claim 1, wherein a reservoir space is formed between an inner wall of the opening of the fuel passage and an outer wall of the outer electrode and is adapted to receive the air bubbles that flow along the upper inner wall of the fuel passage.

4. The fuel sensor according to claim 3, wherein the reservoir space is located between the inner wall of the opening of the fuel passage and the outer wall of the outer electrode and circumferentially extends all around the outer electrode on a radially outer side of the outer electrode.

5. The fuel sensor according to claim 3, wherein the outer electrode includes an annular portion, which is configured into an annular form and radially outwardly protrudes from the blocking portion.

6. The fuel sensor according to claim 1, wherein:

the fuel passage is formed in a flange, which closes an opening of a fuel tank and supports a pump main body that is adapted to draw fuel received in the fuel tank; and the fuel passage conducts the fuel, which is discharged from the pump main body and is to be supplied to an internal combustion engine after passing through the fuel passage.

* * * * *